(12) United States Patent
Colson et al.

(10) Patent No.: US 8,247,559 B2
(45) Date of Patent: Aug. 21, 2012

(54) PROCESS FOR PREPARING AN INTERMEDIATE TO MU OPIOID RECEPTOR ANTAGONISTS

(75) Inventors: Pierre-Jean Colson, San Francisco, CA (US); Ying Yu, Sunnyvale, CA (US); Daniel D. Long, San Francisco, CA (US); Ioanna Stergiades, San Francisco, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

(21) Appl. No.: 13/047,309

(22) Filed: Mar. 14, 2011

(65) Prior Publication Data
US 2011/0166355 A1  Jul. 7, 2011

Related U.S. Application Data

(62) Division of application No. 12/218,383, filed on Jul. 15, 2008, now Pat. No. 7,932,402.

(60) Provisional application No. 60/961,353, filed on Jul. 20, 2007.

(51) Int. Cl.
*C07D 451/02* (2006.01)

(52) U.S. Cl. ...................................... 546/124

(58) Field of Classification Search ................. None
See application file for complete search history.

(56) References Cited

U.S. PATENT DOCUMENTS

| 5,731,317 | A | 3/1998 | Lu et al. |
| 6,680,328 | B2 | 1/2004 | Peters et al. |
| 7,622,508 | B2 | 11/2009 | Long et al. |
| 7,902,220 | B2 * | 3/2011 | Saito et al. ............. 514/304 |
| 2009/0030208 | A1 | 1/2009 | Peters et al. |
| 2009/0137625 | A1 | 5/2009 | Peters et al. |

FOREIGN PATENT DOCUMENTS

| WO | 2004089908 A2 | 10/2004 |
| WO | 2007103187 A2 | 9/2007 |

OTHER PUBLICATIONS

Baxter et al., "Stereoselective Enol Tosylation: Preparation of Trisubstituted .,.-Unsaturated Esters", Organic Letters, vol. 7 No. 2, pp. 215-218 (2005).
Cheng et al., "Stereoselective Syntheses of the Three Isomers of Ethylene Glycol Bis(tropane-3-carboxylate)", Journal of Organic Chemistry, 67, pp. 5433-5436 (2002).
Forbes I. T., "Highly stereoselective synthesis of exo and endo indolotropanes", Tetrahedron Letters, vol. 40 No. 52, pp. 9293-9295 (1999).
Ghosh et al., "Convenient Preparation of Aryl-substituted Nortropanes by Suzuki-Miyaura Methodology", Can. J. Chemistry, 84, pp. 555-560 (2006).
Keverline et al., "Synthesis of the 2beta, 3alpha- and 2beta, 3beta-isomers of 3-(p-substituted phenyl)tropane-2-carboxylic acid methyl esters", Tetrahedron Letters, vol. 36, No. 18, pp. 3099-3102 (1995).
Klapars et al., "Preparation of Enamides via Palladium-Catalyzed Amidation of Enol Tosylates", Organic Letters, vol. 7, No. 6, pp. 1185-1188 (2005).
Lu et al., "Substituted Bridged Phenyl Piperidines: Orally Active Growth Hormone Secretagogues", BioOrganic & Medicinal Chemistry Letters, 13, pp. 1817-1820 (2003).
International Search Report for PCT/US2008/008607.

* cited by examiner

*Primary Examiner* — Kamal Saeed
(74) *Attorney, Agent, or Firm* — Jeffrey A. Hagenah; Roberta P. Saxon

(57) ABSTRACT

The invention provides an efficient method for preparing 3-endo-(8-azabicyclo[3.2.1]oct-3-yl)benzamide by hydrogenation, under controlled conditions, of an amino-protected 3-(8-azabicyclo[3.2.1]oct-2-en-3-yl)benzamide intermediate in which the amino-protecting group is removable by catalytic hydrogenation.

2 Claims, No Drawings

PROCESS FOR PREPARING AN INTERMEDIATE TO MU OPIOID RECEPTOR ANTAGONISTS

CROSS-REFERENCE TO RELATED APPLICATIONS

This application is a divisional application of U.S. Ser. No. 12/218,383, filed Jul. 15, 2008, now allowed; which claims the benefit of U.S. Provisional Application No. 60/961,353, filed on Jul. 20, 2007, the disclosures of which are incorporated herein by reference in their entirety.

BACKGROUND OF THE INVENTION

1. Field of the Invention

The invention is directed to a process for preparing an aryl 8-aza-bicyclo[3.2.1]octane compound which is useful as an intermediate for the preparation of medicinal agents. In particular, the invention is directed to the preparation of intermediates to mu opioid receptor antagonist agents.

2. State of the Art

Compounds that demonstrate antagonism at mu opioid receptors are expected to be useful for treating or ameliorating medical conditions mediated by mu opioid receptor activity, such as disorders of reduced motility of the gastrointestinal tract. For example, such compounds are expected to be useful for the treatment of opioid-induced bowel dysfunction or post-operative ileus. U.S. application Ser. No. 11/711,961 has recently disclosed a series of 3-endo-(8-azabicyclo[3.2.1]oct-3-yl)-(substituted)phenyl compounds, that have exhibited activity as mu opioid receptor antagonists. Of particular interest within this series are compounds of formula (I):

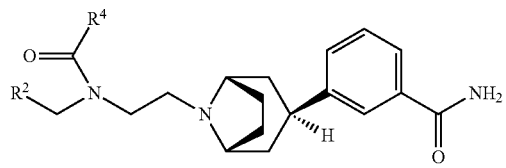

(I)

wherein, for example, $R^2$ is cyclohexyl or 4,4-difluorocyclohexyl, and $R^4$ is $C_{1-4}$alkyl substituted with one or two hydroxyl substituents. As disclosed in the cited application, preparation of such compounds relies on a key intermediate, the compound 3-endo-(8-azabicyclo[3.2.1]oct-3-yl)benzamide:

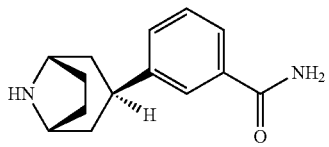

having the endo orientation of the benzamide moiety with respect to the 8-aza-bicylo[3.2.1]octyl group of the final product.

In order to make use of the above class of mu opioid receptor antagonists as medicinal agents, it would be desirable to have an efficient process for preparing 3-endo-(8-azabicyclo[3.2.1]oct-3-yl)benzamide with high stereospecificity. Since the efficiency of the synthesis of organic compounds decreases dramatically with the number of process steps, it would be desirable for the synthetic process to require a minimum number of process steps.

SUMMARY OF THE INVENTION

The present invention provides an efficient method for preparing 3-endo-(8-azabicyclo[3.2.1]oct-3-yl)benzamide. It has been determined that hydrogenation of a 3-(8-azabicyclo[3.2.1]oct-2-en-3-yl)benzamide intermediate provides the product with good selectivity for the desired endo configuration. It has further been determined that under suitable hydrogenation conditions, the product can be prepared in a single step, with good yield and stereoselectivity, from an aryl-8-azabicyclo[3.2.1]oct-2-ene intermediate protected with an amino-protecting group removable by catalytic hydrogenation.

Accordingly, in one aspect, the invention provides a process for preparing a compound of formula 1, having the chemical name 3-endo-(8-azabicyclo[3.2.1]oct-3-yl)benzamide, or a salt thereof:

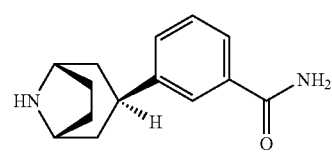

1 the process comprising hydrogenating a compound of formula 2 having the chemical name 3-(8-azabicyclo[3.2.1]oct-2-en-3-yl)benzamide:

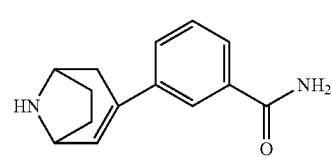

2 or an acid salt thereof, in the presence of a palladium metal catalyst, and, when the compound of formula 2 is in the form of a free base, in the presence of an acid, to provide a compound of formula 1 or a salt thereof.

In another aspect, the invention provides a process for preparing a compound of formula 1 or a salt thereof, the process comprising:

(a) purging a reaction vessel comprising a compound of formula 3:

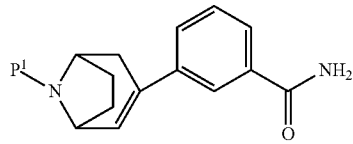

3 and an acid with a non-reactive gas, wherein $P^1$ is an amino-protecting group removable by catalytic hydrogenation, (b) adding a palladium metal catalyst to the reaction vessel;

(c) purging the reaction vessel with hydrogen; and (d) supplying hydrogen gas to the reaction vessel at a pressure of less than about a half atmosphere such that the total pressure in the reaction vessel is less than about one and a half atmospheres to provide a compound of formula 1 or a salt thereof.

In one aspect, the process uses an intermediate of formula 3 in which $P^1$ is benzyl.

In one aspect, the acid is hydrochloric acid.

In another aspect, the process further comprises converting the product of step (d) to a crystalline form.

It has further been established that the intermediate of formula 3 is efficiently prepared in a single step by the reaction of a protected 8-azabicyclo[3.2.1]oct-2-ene intermediate with a substituted phenyl-boronic acid.

In another aspect, therefore, the invention provides a process for preparing a compound of formula 3:

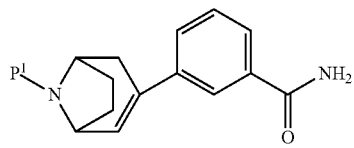

3 wherein $P^1$ is an amino-protecting group, the process comprising:

(a) contacting a compound of formula 5:

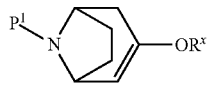

5 wherein —$OR^x$ represents a sulfonate leaving group, with a compound of formula 4:

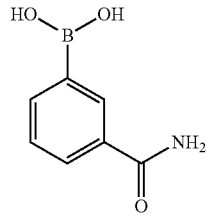

4 in the presence of a palladium catalyst and a phosphine ligand to provide a compound of formula 3.

Based on the above determinations, in a still further aspect, the invention provides a process for preparing a compound of formula 1 or a salt thereof, the process comprising:

(a) contacting a compound of formula 5

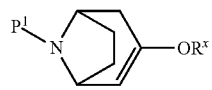

5 wherein $P^1$ is an amino-protecting group removable by catalytic hydrogenation and —$OR^x$ represents a sulfonate leaving group, with a compound of formula 4:

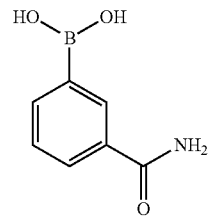

4 in the presence of a palladium catalyst and a phosphine ligand to provide a compound of formula 3:

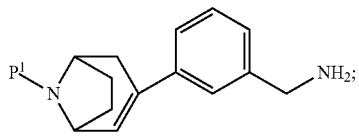

3

(b) purging a reaction vessel comprising a compound of formula 3 and an acid, with a non-reactive gas;
(c) adding a palladium metal catalyst to the reaction vessel;
(d) purging the reaction vessel with hydrogen; and
(e) supplying hydrogen gas to the reaction vessel at a pressure of less than about a half atmosphere such that the total pressure in the reaction vessel is less than about one and a half atmospheres to provide a compound of formula 1 or a salt thereof.

Certain intermediates in the reactions described above are novel. In a composition aspect, therefore, the invention further provides a compound of formula 5 wherein $P^1$ is benzyl and —$OR^x$ represents a sulfonate leaving group, a compound of formula 3 wherein $P^1$ is an amino-protecting group, and a compound of formula 2.

DETAILED DESCRIPTION OF THE INVENTION

A general process for the preparation of 3-endo-(8-azabicyclo[3.2.1]oct-3-yl)benzamide (1) with desirable stereospecificity for the endo orientation is illustrated in the following scheme:

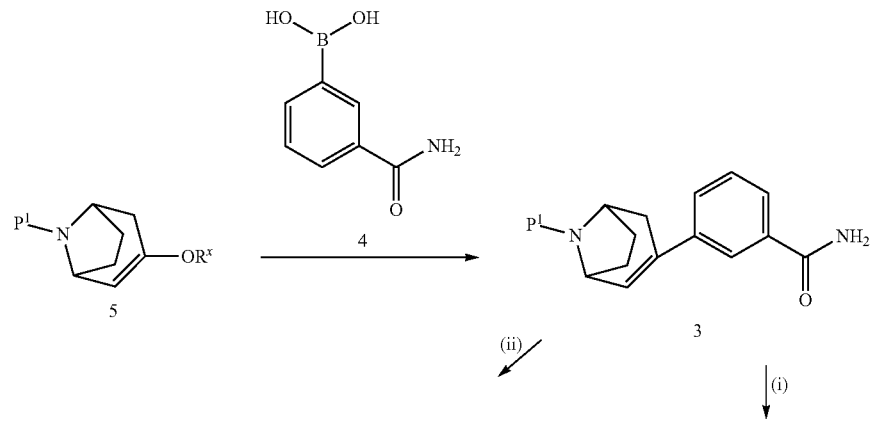

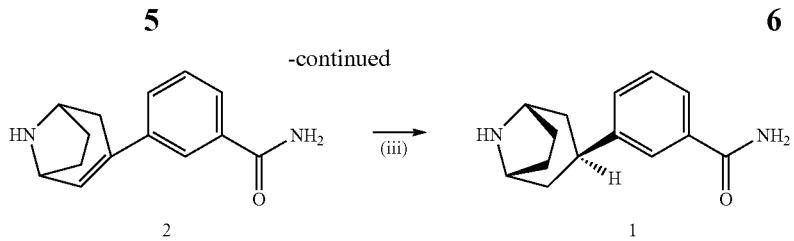

The protected 8-azabicyclo[3.2.1]oct-2-ene (5) where $P^1$ represents an amino-protecting group and —$OR^x$ represents a sulfonate leaving group is a useful starting material. The bicyclooctene intermediate 5 is reacted with a substituted-phenyl-boronic acid 4 to provide intermediate 3. When an amino-protecting group removable by catalytic hydrogenation is used for $P^1$, intermediate 3 can be both deprotected and reduced by catalytic hydrogenation, under controlled conditions, in a single step, as shown in route (i) to provide the product 1. When an amino-protecting group removable by other procedures is used for $P^1$, intermediate 3 is first deprotected to compound 2 (step (ii)) and then hydrogenated (step (iii)) to provide the product 1.

Amino-protecting groups removable by catalytic hydrogenation, typically exposure to hydrogen gas in the presence of a palladium metal catalyst, include, but are not limited to, aryl methyl groups, such as benzyl (Bn), 4-methoxybenzyl, and triphenylmethyl (Tr), and certain carbonyl groups, such as benzyloxycarbonyl (Cbz), p-nitrobenzyloxycarbonyl (PNZ), 2,4-dichlorobenzyloxycarbonyl, and 5-benzisoxazolylmethoxycarbonyl. Amino-protecting groups removable by other procedures, for example treatment with acid, include, but are not limited to, tert-butoxycarbonyl (Boc) and p-methoxybenzyloxycarbonyl (Moz), to name only a few.

Numerous protecting groups, and their introduction and removal, are described in T. W. Greene and G. M. Wuts, *Protecting Groups in Organic Synthesis*, Third Edition, Wiley, New York, 1999, and references cited therein.

The variable —$OR^x$ represents a sulfonate leaving group. Sulfonate leaving groups useful in the present process include trifluoromethane sulfonate (commonly triflate), p-toluene sulfonate (commonly tosylate), and methyl sulfonate (commonly mesylate). Intermediates of formula 5 are conveniently prepared from a protected 8-azabicyclo[3.2.1]octanone 6:

in which $P^1$ is benzyl. For example, as described in detail in the example section below, to prepare a bicyclooctene intermediate 5 in which $P^1$ is benzyl and —$OR^x$ is triflate, benzyl-protected intermediate 6, 8-benzyl-8-azabicyclo[3.2.1]octan-3-one, is contacted with between about 1 and about 1.5 equivalents of N-phenyl-bis(trifluoromethanesulfonimide) and between about 1 and about 1.5 equivalents of a base, such as sodium bis(trimethylsilyl)amide. The reaction is typically conducted at a temperature between about −20 and about −10° C. for between about one half to about two hours, or until the reaction is substantially complete.

To prepare a bicyclootene intermediate 5 in which $P^1$ is Boc and —$OR^x$ is triflate, a Boc-protected intermediate 6 is reacted with N-phenyl-bis(trifluoromethanesulfonimide) and base as described above. The reaction of the Boc intermediate, however, is typically conducted at a lower temperature, less than about −70° C., for between about 2 and about 5 hours, or until the reaction is substantially complete. The Boc-protected intermediate 6 is available commercially or it is prepared by reaction of the benzyl-protected form with di-tert-butyl dicarbonate (commonly $Boc_2O$) and catalytic hydrogenation.

A bicyclooctene intermediate 5 in which $P^1$ is benzyl and —$OR^x$ is tosylate can be prepared from benzyl-protected intermediate 6 by a process analogous to that of the preparation of the benzyl-triflate intermediate, using p-toluenesulfonic acid anhydride (commonly $Tos_2O$) as a reagent.

The benzyl-protected 8-azabicyclo[3.2.1]octanone 6 is typically obtained from commercial sources, and it can be prepared by the reaction of 2,5-dimethoxy tetrahydrofuran with benzylamine and 1,3-acetonedicarboxylic acid in an acidic aqueous solution in the presence of a buffering agent as described in US 2005/0228014. (See also, U.S. Pat. No. 5,753,673).

In the present process, bicyclooctene intermediate 5 is reacted with an aryl boronic acid 4 to provide intermediate 3. Optionally, bicyclooctene 5 can be used as the crude product of the preparation described above without complete isolation and purification. The reaction is typically conducted by contacting 5 with between about 1 and about 1.2 equivalents of 4 in the presence of a catalytic amount of a palladium catalyst and phosphine ligand (between about 0.005 and about 0.1 equivalents), and between about 2 and about 4 equivalents of a base.

Suitable palladium catalysts include tris(dibenzylideneacetone)dipalladium(0) ($Pd_2dba_3$), palladium (II) acetate ($Pd(OAc)_2$), dichloro(1,1'-bis(diphenylphosphino)-ferrocene)dipalladium (Pd(dppf)$Cl_2$), dichloro bis(triphenylphosphine)-palladium (II) (Pd($PPh_3)_2Cl_2$), and the like, where the common abbreviations are given in parentheses. Phosphine ligands useful in the present reaction include tricyclohexylphosphine ($PCy_3$), tricyclohexylphosphine tetrafluoroborate ($PCy_3HBF_4$), 1,1'-bis(diphenylphosphino)-ferrocene (dppf), 1,1'-bis(di-tert-butylphosphino)ferrocene, tri(2-furyl)phosphine, 1,3-bis(diphenylphosphino)propane (dppp), 1,5-bis(diphenylphosphino)pentane (dpppe), tri-tert-butylphosphine (P(t-Bu)$_3$), and 9,9-dimethyl-4,5-bis(diphenylphosphino)xanthene (Xantphos). The following are exemplary catalyst systems for the boronic acid coupling reaction: 0.01 equivalent $Pd(OAc)_2$/0.01 equivalent dppf, 0.04 equivalent $Pd_2 dba_3$/0.08 equivalent $PCy_3HBF_4$, 0.03 equivalent $Pd_2 dba_3$/0.06 equivalent dpppe.

Typical bases for the coupling reaction include potassium fluoride and cesium fluoride. Alternatively, cesium carbonate, sodium carbonate, potassium carbonate, sodium acetate, potassium tert-butoxide, 1,8-diazabicyclo[5.4.0]undec-7-ene (DBU), or 1,4-diazabicyclo[2.2.2]octane (DABCO) can be used for the base. The reaction is typically conducted in an inert diluent, such as tetrahydrofuran, N,N-dimethylformamide, N,N-dimethyacetamide, or N-methylpyrrolidone. Suitable mixed solvent systems include tetrahydrofuran and water, tetrahydrofuran and N,N-dimethylformamide, tetrahydrofuran and N-methylpyrrolidone, acetone and water, ethanol and water, and isopropanol and water. The reaction is typically conducted at a temperature of between about 40 and about 80° C. for about 1 to about 4 hours or until the reaction is substantially complete. The product 3 is isolated as a solid by conventional procedures. Optionally, product 3 can be further purified by isolation as an acid salt, typically a hydrochloride salt.

Next, when $P^1$ is an amino-protecting group removable by catalytic hydrogenation, the protected 3-(8-azabicyclo[3.2.1]oct-3-en-3-yl)benzamide intermediate 3 is deprotected and reduced in a single hydrogenation step, as indicated schematically in route (i), to provide the product 1. In the hydrogenation reaction, a reaction mixture of intermediate 3 in an alcoholic diluent, for example ethanol and water, and, between about 1.5 and about 2.5 equivalents of an acid, for example, hydrochloric acid, is first purged with a non-reactive gas to reduce the amount of oxygen in the reaction mixture. Typically, nitrogen is used as the purging gas although argon or other inert gas may alternatively be employed. Purging is typically performed by providing the gas through a tube inserted in the reaction mixture, which is contained in a vessel open to the atmosphere. It has been observed that it is advantageous to limit the amount of time the reaction mixture is exposed to the purging gas. For example, for a reaction at the 40 gram scale using a one liter hydrogenation vessel, a good rate of conversion to product is achieved when the reaction mixture is initially purged with nitrogen for about 5 to about 10 minutes. If the initial flow of nitrogen is longer than about one half hour, the rate of conversion to product is expected to be adversely affected.

Then, a palladium metal catalyst, conventionally palladium on carbon, is added, and the reaction mixture is purged with hydrogen, as described above, which has the effect of introducing hydrogen into the reaction mixture, replacing at least some of the purging gas. The length of time required to introduce hydrogen into the reaction mixture depends on the scale of the reaction. For example, for reaction at the 40 gram scale, it is beneficial to purge with hydrogen for about 5 to about 10 minutes, but a longer period has been found to be detrimental. For reaction at the kilogram scale, it is expected to be useful to purge the reaction mixture with hydrogen for about 20 to about 30 minutes. Next, a flow of hydrogen gas at less than about one half atmosphere is applied to the reaction mixture, typically in a closed vessel, such that the total pressure in the vessel is less than about one and a half atmospheres. The reaction is typically conducted at a temperature of between about 45 and about 55° C. for between about 3 and about 6 hours or until the reaction is substantially complete. Including an acid in the reaction mixture, provides the product as the acid salt.

It has been observed that the results of the hydrogenation reaction depend on the pressure with which hydrogen gas is supplied. Limiting the applied hydrogen pressure to below about one half atmosphere promotes both the selectivity for the desired endo orientation of the product and the rate of reaction. Using the controlled hydrogenation conditions described here, the percentage of exo material in the product is no more than about 10%, typically between about 6 and about 10%. For example, as described below, the reaction of benzyl-protected intermediate 3 in which the applied hydrogen gas pressure was kept below 5 pounds per square inch (psi) (0.34 atmosphere) resulted after 5 hours in >99% conversion to the hydrochloride salt of the product 1 with an endo:exo isomer ratio of about 93:7.

In contrast, exposure to a flow of hydrogen gas of 20 psi (1.36 atmospheres) above atmospheric pressure for 40 hours, resulted in ~95% conversion to the product 1 with an endo:exo isomer ratio of about 85:15.

In one aspect, therefore, the invention provides a process of preparing a compound of formula 1 or a salt thereof, wherein the step of supplying hydrogen gas is supplying hydrogen gas at a pressure controlled such that the percentage of exo isomer in the product 1 is less than about 10%.

When $P^1$ is a an amino-protecting group that is not removed by catalytic hydrogenation, first the protecting group is removed by the appropriate conventional procedure to provide intermediate 2, which is then hydrogenated to provide the product 1. For example when $P^1$ is Boc, intermediate 3 is contacted with trifluoroacetic acid to provide 2 as the trifluoroacetate salt. When intermediate 2 is provided as an acid salt, it is not necessary to add additional acid in the hydrogenation step. Hydrogenation of the deprotected intermediate 2 provides the product 1 with acceptable stereoselectivity and does not appear to be very sensitive to hydrogenation conditions. In this process, as well, the percentage of exo material in the product is generally no more than about 10%, typically between about 6 and about 10%. For example, treatment of 2 under a balloon of hydrogen (approximately one atmosphere) resulted in the product 1 with an endo:exo isomer ratio of about 93:7. This observation is consistent with the hypothesis that limiting the hydrogen pressure in the hydrogenation reaction of intermediate 3 when $P^1$ is removable by catalytic hydrogenation, as described above, favors deprotection of 3 over reduction of the double bond.

Finally, the stereo selectivity of the product of the hydrogenation reaction can be further improved by crystallization as an acid salt, for example, as the hydrochloride salt. The crude product of the hydrogenation reaction is crystallized by conventional procedures. For example, to crystallize the product as the hydrochloride salt, a mixture of the crude product, between about 1.5 and about 2.5 equivalents of hydrochloric acid, if not present in the hydrogenation reaction, and an alcohol, preferably the alcohol used as a diluent in the previous step, is heated to about 60° C. until complete dissolution of any solids is obtained. The crystallization reaction mixture is cooled with stirring to about 35° C., then to about room temperature and is stirred at about 0° C. for about one hour to about 6 hours or until crystallization is substantially complete.

Optionally, to promote crystallization, seed crystals of the product are added when the temperature of the mixture is about 35° C. Addition of an antisolvent, such as methyl tert-butyl ether (MTBE), when the mixture is at room temperature is advantageous for improving the yield. Including the crystallization procedure, the hydrochloride salt of compound 1, for example, has been obtained with a percentage of the undesired exo isomer of less than about 0.5%.

In the event, the product of hydrogenation has an unacceptably large exo component, e.g. the hydrogenation step failed to use a controlled pressure of hydrogen gas, a modified crystallization procedure can be used to improve the stereospecificity to about the level described above. The modified procedure uses a longer crystallization period. A mixture of the crude product and an alcohol is heated to about 60° C. until complete dissolution is observed and then cooled to about 30° C. at which temperature seed crystals of the product are added. A useful ratio of seed crystals to crude product is between about 1:800 and about 1:400 (weight:weight). The resulting slurry is cooled to room temperature and stirred for between about 8 and about 24 hours until a crystalline precipitate is observed and then an antisolvent, in particular, 2-methyl tetrahydrofuran is added. The slurry is typically stirred for another period of between about 3 and about 6 hours, or until precipitation is substantially complete. The crystals are isolated by conventional methods. Using this procedure, the hydrochloride salt of compound 1 with an exo component of less than about 2%, including less than about 1% and less than about 0.5%, can be obtained from a crude product with an exo component of about 15%.

EXAMPLES

The following synthetic examples are offered to illustrate the invention, and are not to be construed in any way as limiting the scope of the invention. In the examples below, the following abbreviations have the following meanings unless otherwise indicated. Abbreviations not defined below have their generally accepted meanings.

ACN=acetonitrile
DMF=N,N-dimethylformamide
EtOAc=ethyl acetate
EtOH=ethanol
NaHMDS=sodium bis(trimethylsilyl)amide
MeTHF=2-methyltetrahydrofuran
MTBE=tert-butyl methyl ether
psi=pounds per square inch
Rt=retention time Reagents and solvents were purchased from commercial suppliers (Aldrich, Strem Chemicals, Inc., etc.), and used without further purification. Progress of reaction mixtures was monitored by analytical high performance liquid chromatography and mass spectrometry. Endo/exo ratios of products were determined by HPLC analysis using the protocols described below. Reaction mixtures were worked up as described specifically in each reaction; commonly they were purified by extraction and other purification methods such as temperature-, and solvent-dependent crystallization, and precipitation. Characterization of reaction products was routinely carried out by mass and $^1$H-NMR spectrometry. For NMR measurement, samples were dissolved in deuterated solvent (DMSO-$d_6$ or CDCl$_3$), and $^1$H-NMR spectra were acquired with a Varian Gemini 2000 instrument (400 MHz) under standard observation conditions. Mass spectrometric identification of compounds was performed using an Agilent (Palo Alto, Calif.) model 1100 LC/MSD instrument.

General HPLC Conditions
   Column: Zorbax SB-Aq, 5 µm. 4.6×250 mm
   Column temperature: 40° C.
   Flow rate: 1.0 mL/min
   Mobile Phases: A=Water/ACN (98:2)+0.1% TFA
   B=Water/ACN (10:90)+0.1% TFA,
   Injection volume: 10 µL
   Detector wavelength: 214 nm HPLC Method 1
   Crude compounds were dissolved in Water/ACN (50:50) at about 1 mg/mL and analyzed using the following gradient over 20 min (time (min)/% B): 0/10, 2.5/20, 9/75, 15/90, 17/90, 18/10, 20/10.

HPLC Method 2
   Compounds were dissolved in Water/ACN (90:10) at about 1 mg/mL and analyzed using the following gradient over 30 min (time (min)/% B): 0/10, 13/10, 23/65, 28/90, 29/90, 30/10.

HPLC Method 3
   Compounds were dissolved in Water/ACN (90:10) at about 1 mg/mL and analyzed using the following gradient over 55 min (time (min)/% B): 0/10, 10/20, 46/75, 47/90, 50/10, 55/10.

Example 1

Synthesis of
3-endo-(8-azabicyclo[3.2.1]oct-3-yl)benzamide
hydrochloride a. Preparation of trifluoro-methanesulfonic acid
8-benzyl-8-azabicyclo[3.2.1]oct-2-en-3-yl ester To a 500 mL flask was added 8-benzyl-8-azabicyclo[3.2.1]octan-3-one hydrochloride (50.4 g, 200 mmol), EtOAc (160 mL), and 4 N NaOH (50 mL). The reaction mixture was heated to 30° C. and stirred at that temperature for 1 h. The layers were separated and the aqueous layer was discarded. The volume of the organic layer was reduced to ~40 mL by rotary evaporation and THF (270 mL) was added.

The resulting solution was added to a 1 L flask and cooled to −20° C. A NaHMDS solution (1 M in THF, 230 mL, 230 mmol) was added to the flask over 15 min. The reaction mixture was stirred at −20±5° C. for 1 h. N-phenyl-bis(trifluoromethanesulfonimide (82.2 g, 230 mmol) was added to the reaction mixture in portions over 5 min and the mixture was stirred at −20° C. to −10° C. for 1 h. To the reaction mixture was added 1 N NaOH (200 mL) and the mixture was allowed to warm to 22° C. with stirring. Solvent was partially removed by rotary evaporation at 30° C. to a volume of 450 mL. To the remaining reaction mixture was added EtOAc (300 mL) and heptane (150 mL). The mixture was stirred at 22° C. for 5 min. The layers were separated and the aqueous layer was discarded. The organic layer was washed with 1N NaOH (3×450 mL). The aqueous layers were discarded. The organic layer was concentrated by rotary evaporation to provide the title intermediate (77 g, >96% purity by HPLC method 1).

$^1$H NMR (d$_6$-DMSO, 400 MHz): δ (ppm) 7.25-7.35 (m, 5H), 6.05 (d, J=5.2, 1H), 3.64 (q, J=13.2, 2H), 3.40-3.44 (m, 2H), 2.77 (d, J=16.4, 1H), 1.79-2.09 (m, 5H), 1.52-1.59 (m, 1H).

b. Preparation of 3-(8-benzyl-8-azabicyclo[3.2.1]oct-2-en-3-yl)benzamide

To the crude product of the previous step was added THF (420 mL) and the solution was purged with nitrogen for 5 min. To a 2 L flask was added 3-carbamoylphenyl boronic acid (98%, 33.0 g, 200 mmol), palladium (II) acetate (98%. 0.46 g, 2 mmol), 1,1'-bis(diphenylphosphino)ferrocene (97%, 1.1 g, 2 mmol). and potassium fluoride (34.9 g, 600 mmol) followed by the THF solution of trifluoro-methanesulfonic acid 8-benzyl-8-aza-bicyclo[3.2.1]oct-2-en-3-yl ester. The resulting mixture was purged with nitrogen for 5 min, heated to reflux (67° C.) under nitrogen and stirred for 2 h. The reaction mixture was cooled to 30° C., then EtOAc (500 mL) and 1 N NaOH (500 mL) were added and the mixture was stirred at 22° C. for 10 min. The layers were separated and the aqueous layer was discarded. The organic layer was washed with a mixture of brine (250 mL) and water (250 mL) and stirred for 5 min. The layers were separated and the aqueous layer was discarded. The organic layer was briefly dried over Na$_2$SO$_4$, filtered, and solvent was partially removed. Product precipitated as light yellow solids during solvent removal. The resulting slurry (about 200 mL) was filtered and the solids were washed with cold EtOAc (0° C., 100 mL) and dried under high vacuum at 25° C. to provide the title intermediate (42.5 g) as a light yellow solid.

The mother liquor and the above washes were combined and concentrated and the resulting slurry (about 100 mL) was stirred at 5° C. for 30 min and filtered. The filtered solids were washed with cold EtOAc (0° C., 30 mL) and dried under high vacuum to provide a second crop of the title intermediate (7 g, combined yield 78%, >98.5% pure by HPLC method 1).

(m/z): [M+H]$^+$ calcd for $C_{21}H_{22}N_2O$, 319.18. found 319.4. $^1$H NMR (CDCl$_3$, 400 MHz): δ (ppm) 7.9 (s, 1H), 7.63 (d, J=6.4, 1H), 7.57 (d, J=6.4, 1H), 7.21-7.42 (m, 6H), 6.38 (d, J=4.4, 1H), 6.13 (s, br, 1H), 5.83 (s, br, 1H), 3.68-3.76 (m, 2H), 3.46-3.51 (m, 2H), 2.92 (d, J=17.2, 1H), 2.18-2.26 (m, 1H), 2.04-2.12 (m, 2H), 1.86-1.92 (m, 1H), 1.58-1.65 (m, 1H).

c. Synthesis of 3-endo-(8-azabicyclo[3.2.1]oct-3-yl)benzamide hydrochloride

To a 1 L hydrogenation vessel was added 3-(8-benzyl-8-azabicyclo[3.2.1]oct-2-en-3-yl)benzamide (40 g, 125 mmol), EtOH (800 mL), 6 M HCl (42 mL) and water (80 mL) and the mixture was stirred at 22° C. until complete dissolution was observed. The reaction mixture was purged with nitrogen for 5 min while being heated to 30° C. over 5 min. To the mixture was added 10 wt % Pd/C (50% in water, 4 g). The mixture was purged at atmospheric pressure with hydrogen for 5-10 min while being heated. The mixture was stirred at 50° C. under a flow of hydrogen at <5 psi (<0.34 atmospheres) for 5 h, resulting in >99% conversion of the reactants, according to HPLC analysis. The solution was cooled to 30° C. and filtered through Celite to provide a solution of the crude title compound with an endo:exo ratio of ~93:7 by HPLC method 2 endo Rt=10.97, exo Rt=12.67. (m/z): [M+H]$^+$ calcd for $C_{14}H_{18}N_2O$, 231.15. found 231.2.

Water was removed from the crude product by azeotropic distillation at 30° C. in EtOH (~80 mL) to provide a slurry that was heated to 60° C. until complete dissolution. The solution was cooled to 35° C. and seed crystals of the product (0.05 g) were added. (The seed crystals were prepared according to the process described in U.S. application Ser. No. 12/072,534.) The resulting slurry was stirred at 22° C. for 30 min, MTBE (120 mL) was added slowly, and the slurry was stirred at 22° C. for 4 h and then at 0° C. for 1 h. The resulting solids were filtered, washed with cold EtOH and dried under high vacuum to provide the title compound (24.5 g) as a white powder (75% yield, >98.5% purity <0.4% exo isomer by HPLC method 3, endo Rt=8.67, exo Rt=9.43).

(m/z): [M+H]$^+$ calcd for $C_{14}H_{18}N_2O$ 231.15. found 231.2. $^1$H NMR (d$_6$-DMSO, 400 MHz): δ (ppm) 9.13 (s, br, 1H), 9.03 (s, br, 1H), 8.05 (s, 1H), 7.93 (s, 1H), 7.73 (d, J=7.6, 1H), 7.58 (d, J=7.6, 1H), 7.40 (t, J=7.6, 2H), 3.97 (s, 2H), 117-3.23 (m, 1H), 2.39-2.46 (m, 2H), 2.19-2.24 (m, 2H), 1.86-1.89 (m, 2H), 1.59-1.63 (m, 2H).

Example 2

Synthesis of 3-endo-(8-azabicyclo[3.2.1]oct-3-yl)benzamide hydrochloride a. Preparation of 3-oxo-8-azabicyclo[3.2.1]octane-8-carboxylic acid tert-butyl ester To a 1 L hydrogenation vessel was added 8-benzyl-8-azabicyclo[3.2.1]octan-3-one (86.1 g, 400 mmol), di-tert-butyl dicarbonate (98.2 g, 450 mmol), 10 wt % NYC (24 g, 11 mmol) and EtOAc (400 mL). The suspension was stirred and purged with nitrogen for 10 min. The reaction mixture was stirred under 50 psi hydrogen (3.4 atmospheres) at 20° C. for 28 h. The reaction mixture was then filtered through Celite. The wet solid cake was washed with EtOAc (100 mL). The filtrate and washes were combined and saturated NaHCO$_3$/brine (1:1 mixture, 400 mL) was added. The EtOAc solution was separated, dried over Na$_2$SO$_4$, and concentrated to yield a light yellow sticky oil which solidified upon standing to give the title intermediate (93 g, quantitative yield).

$^1$H NMR (CDCl$_3$, 400 MHz): δ (ppm) 4.47 (s, br, 2H), 2.63 (s, br, 2H), 2.32 (d, J=16.4, 2H), 2.08 (m, 2H), 1.65 (t, J=8, 2H), 1.49 (s, 9H).

b. Preparation of 3-trifluoromethanesulfonyloxy-8-azabicyclo[3.2.1]oct-2-ene-8-carboxylic acid tert-butyl ester To a 1 L flask was added the product of the previous step (93 g, 400 mmol) and THF (400 mL). The mixture was stirred at room temperature until complete dissolution was observed, and then was cooled to −74° C. A NaHMDS solution (1 M in THF, 460 mL, 460 mmol) was added slowly to the reaction vessel over 3 h (temp<−70° C.). N-phenyl-bis(trifluoromethanesulfonimide) (164 g, 460 mmol) was added to the reaction mixture in portions while maintaining the internal temperature<−70° C. Additional THF (200 mL) was added and the mixture was stirred at −74° C. for 90 min. The mixture was warmed to room temperature and slightly concentrated to remove about 200 mL solvent. To the remaining solution was added 1N NaOH (600 mL), hexanes (200 mL) and EtOAc (400 mL). The layers were separated and the organic layer was washed with 1 N NaOH (3×200 mL) and brine (200 mL), dried over Na$_2$SO$_4$, and then concentrated. The residue was dried and slowly solidified to give the title intermediate as yellowish solids (117.8 g, 82% yield).

$^1$H NMR (d$_6$-DMSO, 400 MHz): δ (ppm) 6.32 (d, J=6, 1H), 4.30-4.40 (m, 2H), 2.90 (d, J=16.4, 2H), 2.18-2.23 (m, 2H), 1.91-1.98 (m, 2H), 1.65-1.72 (m, 2H), 1.39 (s, 9H).

c. Preparation of 3-(3-carbamoylphenyl)-8-azabicyclo[3.2.1]oct-2-ene-8-carboxylic acid tert-butyl ester To a 250 mL flask was added 3-trifluoromethanesulfonyloxy-8-azabicyclo[3.2.1]oct-2-ene-8-carboxylic acid tert-butyl ester (20 g, 56 mmol), 3-carbamoylphenyl boronic acid (10.2 g, 61 mmol), tris(dibenzylideneacetone)dipalladium(0) (Pd$_2$ dba$_3$) (2 g, 2.2 mmol), tricyclohexylphosphine tetrafluoroborate (PCy$_3$HBF$_4$) (1.65 g, 4.4 mmol) and KF (9.8 g, 168 mmol). The reagents were purged with nitrogen for 5 min, and then THF (120 mL) and DMF (30 mL) was added. The suspension was stirred and purged with nitrogen for another 5 min, then heated to 70° C. After 2 h at 70° C., the mixture was cooled to room temperature and filtered through Celite. The filtrate was concentrated and the residue was partitioned between EtOAc (350 mL) and 0.5 N NaOH (400 mL)/brine (50 mL). The organic layer was separated and dried with Na$_2$SO$_4$. A quarter of the solution was removed. The remainder of the solution was concentrated to ~100 mL to which hexanes (50 mL) was added. Solid precipitates were observed. The solution volume was reduced by 10 mL, hexanes (10 mL) was added, and the slurry was stirred at 0° C. for 1 h. The solids were filtered and dried to give the title intermediate (8.4 g) as light yellow solids. The mother liquor was further concentrated to give more solid precipitate, which was filtered to provide additional product (0.5 g). (Combined 66% yield).

$^1$H NMR (d$_6$-DMSO, 400 MHz): δ (ppm) 8.01 (s, 1H), 7.89 (t, J=1.6, 1H), 7.73-7.76 (m, 1H), 7.55 (d, J=8, 1H), 7.36-7.42

(m, 2H), 6.62 (d, J=5.2, 1H), 4.35-4.41 (m, 2H), 2.95-2.99 (m, 1H), 1.65-2.33 (m, 5H), 1.38 (s, 9H).

d. Preparation of 3-(8-azabicyclo[3.2.1]oct-2-en-3-yl)benzamide

To a 50 mL flask was added 3-(3-carbamoylphenyl)-8-azabicyclo[3.2.1]oct-2-ene-8-carboxylic acid tert-butyl ester (4 g, 12 mmol) and TFA (10 mL). The mixture was stirred at room temperature for 30 min. The solution was concentrated and the residue was dried under vacuum. Crystalline solids were observed in the reaction mixture, which was then stirred in THF (~10 mL) at 0° C. for 1 h. The solids were filtered to provide the TFA salt of the title intermediate (2.4 g) as light yellow solids. Additional product (0.32 g) was recovered from the mother liquor (Combined 66% yield).

$^1$H NMR ($d_6$-DMSO, 400 MHz): 8.96 (s, br, 2H), 8.05 (s, 1H), 7.96 (s, 1H), 7.82 (d, J=7.6, 1H), 7.62 (d, J=7.6, 1H), 7.42-7.48 (m, 2H), 6.54 (d, J=6, 1H), 4.29-4.38 (m, 2H), 3.03-3.08 (m, 2H), 2.65 (d, J=18, 1H), 2.05-2.22 (m, 3H), 1.83-1.89 (m, 1H).

e. Synthesis of 3-endo-(8-azabicyclo[3.2.1]oct-3-yl)benzamide hydrochloride

To a 25 mL flask was added 3-(8-azabicyclo[3.2.1]oct-2-en-3-yl)benzamide trifluoroacetate (0.25 g, 0.7 mmol), EtOH (5 mL) and water (0.5 mL). The mixture was stirred at room temperature and purged with nitrogen. To the solution was added 10 wt % Pd/C (0.025 g) and the mixture was purged with hydrogen for 5 min. Then the mixture was heated to 50° C. and stirred under a balloon of hydrogen for 16 h. The mixture was cooled to room temperature and filtered through Celite. The filter cake was washed with EtOH (10 mL) and the liquors were combined and concentrated to about 1 mL to provide crude title product with an endo/exo isomer ratio of 93:7 by HPLC method 3 endo Rt=8.67, exo Rt=9.43. (m/z): [M+H]$^+$ calcd for $C_{14}H_{18}N_2O$ 231.15. found 231.4.

To the crude product was added concentrated HCl (~0.1 mL) and the reaction mixture was heated to 60° C. until complete dissolution. The solution was cooled to 35° C. and seed crystals (about 2 mg) were added. (The seed crystals were obtained as described in Example 1.) The slurry was further cooled to room temperature and MTBE (2 mL) was added. The slurry was stirred at room temperature for ~2 h then at 0° C. for 30 min. The solid was filtered to provide the title compound (~0.13 g, <0.4% exo isomer by HPLC method 3 endo Rt=8.67, exo Rt=9.43). (m/z): [M+H]$^+$ calcd for $C_{14}H_{18}N_2O$ 231.15. found 231.4.

Example 3

Synthesis of 3-(8-benzyl-8-azabicyclo[3.2.1]oct-2-en-3-yl)-benzamide a. Preparation of toluene-4-sulfonic acid 8-benzyl-8-azabicyclo[3.2.1]oct-2-en-3-yl ester To a 1 L flask was added 8-benzyl-8-azabicyclo[3.2.1] octan-3-one (12.9 g, 60 mmol) and THF (100 mL). The mixture was stirred at room temperature until complete dissolution was observed, and then was cooled to −30° C. Lithium-bis-(trimethylsilyl)amide (LiHMDS) solution (1 M in THF, 69 mL, 69 mmol) was added to the reaction solution over 30 min. The solution was stirred at −25±5° C. for 1 h. A solution of p-toluene sulfonic acid anhydride (22.5 g, 69 mmol) in THF (150 mL) was added to the reaction mixture at a temperature of −7±3° C. The resulting solution was stirred at −10° C. to 10° C. for 1 h. To the solution was added EtOAc (250 mL) and 1 N NaOH (200 mL) and the solution was stirred at room temperature for 5 min. The organic layer was separated and washed with 0.5 N NaOH (200 mL) followed by 1:1 brine:water (200 mL). The organic layer was dried over $Na_2SO_4$, and concentrated to give a yellow solid residue. The solids were slurried in hexane (40 mL)/trace EtOAc(<5 mL) and filtered to provide the title intermediate (19.1 g, 86% yield).

(m/z): [M+H]$^+$ calcd for $C_{21}H_{23}NO_3S$ 370.15. found 370.2. $^1$H NMR (CDCl$_3$, 400 MHz): δ (ppm) 7.84-7.86 (m, 2H), 7.21-7.37 (m, 7H), 5.4 (dt, J=5.6, 1.6, 1H), 3.58 (d, J=1.2, 2H), 3.24-3.32 (m, 2H), 2.58-2.63 (m, 1H), 2.46 (s, 3H), 2.05-2.13 (m, 1H), 1.89-1.95 (m, 1H), 1.70-1.77 (m, 2H), 1.41-1.49 (m, 1H).

b. Synthesis of 3-(8-benzyl-8-azabicyclo[3.2.1]oct-2-en-3-yl)-benzamide

To a 100 mL round bottom flask was added toluene-4-sulfonic acid 8-benzyl-8-azabicyclo[3.2.1]oct-2-en-3-yl ester (0.75 g, 2 mmol), 3-carbamoylphenyl boronic acid (0.36 g, 2.2 mmol), Pd$_2$dba$_3$ (0.055 g, 0.06 mmol), 1,5-bis(diphenylphosphino)pentane (0.053 g, 0.12 mmol) and CsF (0.91, 6 mmol). The reaction mixture was purged with nitrogen for 5 min, and THF (8 mL) and 1.5 mL DMF (1.5 mL) were added. The suspension was stirred at room temperature and purged with nitrogen for another 5 min, then heated to 68° C. After 21 h at 68° C., the reaction mixture was cooled to room temperature and partitioned between EtOAc (20 mL) and 1 N NaOH (20 mL). The organic layer was washed with 1:1 brine:water (2×20 mL) and dried over Na$_2$SO$_4$. The organic layer was concentrated to 7 to 8 mL, resulting in a slurry that was filtered to provide the title compound (0.41 g, 64% yield) as off-white solids. (m/z): [M+H]$^+$ calcd for $C_{21}H_{22}N_2O$, 319.18. found 319.4.

Example 4

Synthesis of 3-endo-(8-azabicyclo[3.2.1]oct-3-yl)benzamide hydrochloride a. Synthesis of 3-endo-(8-azabicyclo[3.2.1]oct-3-yl)benzamide hydrochloride To a hydrogenation vessel was added 3-(8-benzyl-8-azabicyclo[3.2.1]oct-2-en-3-yl)benzamide (5 g, 15.7 mmol), EtOH (100 mL), and 6 N HCl (7.5 mL). The mixture was stirred at room temperature and was purged with nitrogen for 5 min. To the solution was added 10 wt % Pd/C (0.5 g) and the mixture was purged with hydrogen for 5 min. The mixture was heated to 50° C. and stirred at that temperature under a flow of hydrogen at 20 psi (1.36 atmosphere) for 40 h, resulting in about 95% conversion to the title compound with an endo/exo isomer ratio of 85:15 according to HPLC method 2 (endo Rt=10.97, exo Rt=12.67). The mixture was cooled to room temperature and filtered through Celite. The mother liquor was concentrated to give the crude title product.

b. Crystallization of 3-endo-(8-azabicyclo[3.2.1]oct-3-yl)benzamide hydrochloride To the crude product of the previous step was added EtOH (20 mL), and the reaction mixture was heated to 60° C. until complete dissolution. The solution was cooled to 30° C. at which time seed crystals of the title compound (about 10 mg) were added. (The seed crystals were obtained as described in Example 1.) The slurry was cooled to room temperature with stirring and stirred overnight at room temperature. Crystal precipitates were observed. To the slurry was added MeTHF (15 mL) and the slurry was stirred at room temperature for another 4 h and filtered to provide the title compound (2.1 g, 50% yield, 0.3% exo isomer by HPLC method 2 (endo Rt=10.97, exo Rt=12.67)).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A compound of formula 2

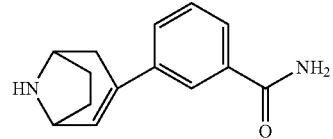

2 having the chemical name 3-(8-azabicyclo[3.2.1]oct-2-en-3-yl)benzamide.

2. A compound of formula 3:

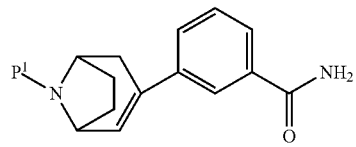

3 wherein $P^1$ is tert-butoxycarbonyl.

* * * * *